United States Patent [19]

Gagne et al.

[11] Patent Number: 4,509,688
[45] Date of Patent: Apr. 9, 1985

[54] ONE-PIECE NEBULIZER JET

[75] Inventors: Roger A. Gagne, Los Angeles; Rolf O. Orchard, Manhattan Beach, both of Calif.

[73] Assignee: Puritan-Bennett Corporation, Los Angeles, Calif.

[21] Appl. No.: 327,487

[22] Filed: Dec. 4, 1981

[51] Int. Cl.³ ............................................. A61M 11/00
[52] U.S. Cl. ................................ 239/338; 128/200.18; 128/200.21; 239/600; 261/DIG. 65
[58] Field of Search ............... 239/338, 343, 370, 600; 128/200.18, 200.21; 261/78 A, DIG. 65

[56] References Cited

U.S. PATENT DOCUMENTS

| 628,561 | 7/1899 | Strakosch | 239/600 |
| 3,240,434 | 3/1966 | Bradley | 239/600 |
| 3,724,454 | 4/1973 | Brown | 128/200.18 |
| 3,744,722 | 7/1973 | Burns | 239/338 |
| 3,857,909 | 12/1974 | Huggins | 128/200.18 |
| 4,100,235 | 7/1978 | Thornwald | 261/DIG. 65 |

Primary Examiner—John J. Love
Assistant Examiner—Michael J. Forman
Attorney, Agent, or Firm—Fulwider, Patton, Rieber, Lee & Utecht

[57] ABSTRACT

A nebulizer jet (10) having complementary portions (12 and 14) molded as a single part and joined by an integral hinge (16) for ease and precision of assembly. When the complementary portions are folded together about the hinge, they form a nebulizer chamber (22) with a jet inlet port (32), a liquid inlet tube (36), and an outlet port (34). A fractionating ball (40) is also molded integrally with the nebulizer jet, and is folded about another integral hinge (44) and secured in an operative position adjacent to the outlet port.

3 Claims, 7 Drawing Figures

U.S. Patent  Apr. 9, 1985  4,509,688
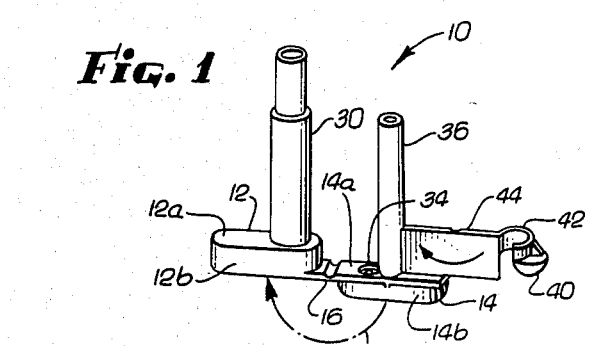
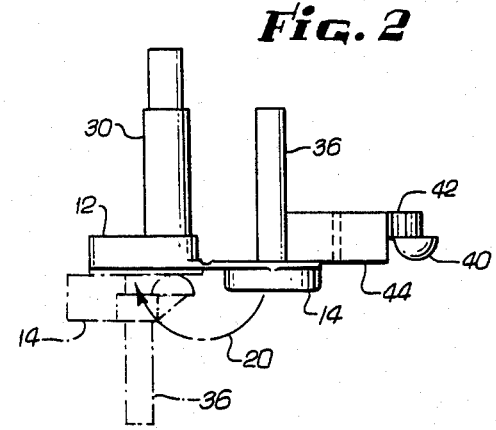
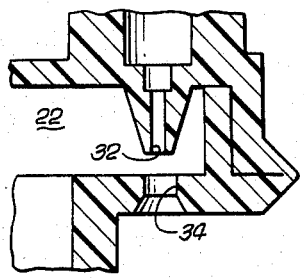
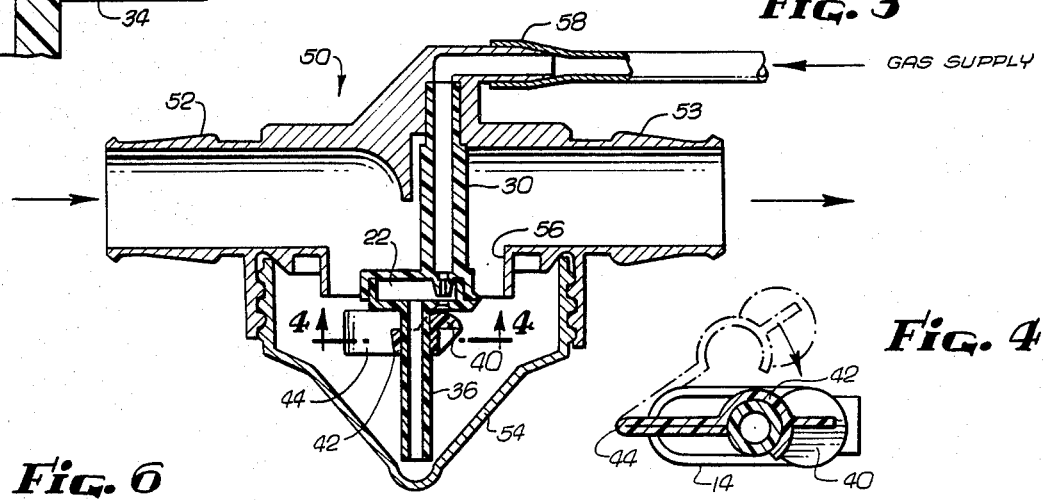
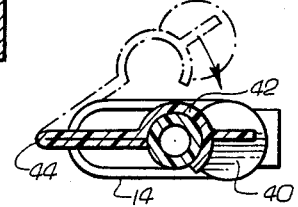
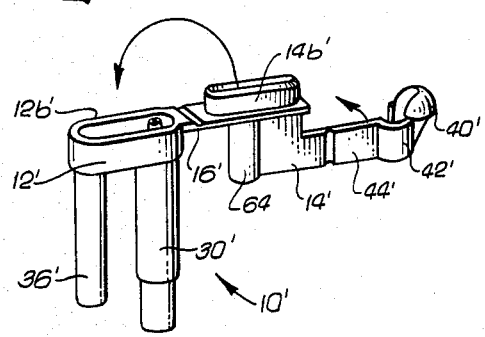
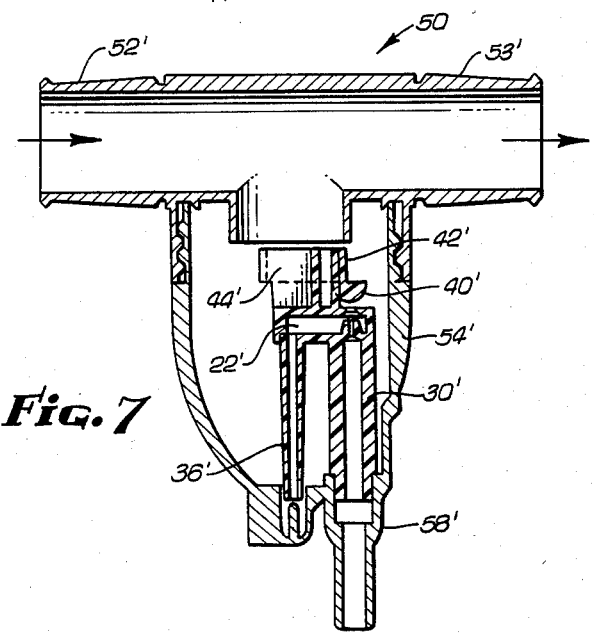

ONE-PIECE NEBULIZER JET

BACKGROUND OF THE INVENTION

This invention relates generally to nebulizer jets of the type used, in conjunction with respirators, to create an aerosol consisting of air and a liquid, usually water and a medicinal substance intended for inhalation into a patient's lungs. More particularly, the invention relates to disposable nebulizer jets of this general type.

Basically, a nebulizer jet includes a small closed structure forming a nebulizer chamber. The chamber has a jet inlet port, a liquid inlet port, and an outlet port, the jet inlet port being axially aligned with the outlet port. A jet of air or other gas enters the chamber through the jet inlet port and draws a mixture of gas and liquid out through the outlet port. The liquid inlet port is connected by a tube to a supply of a liquid medicinal substance, which is drawn into the chamber by action of the jet flow. The nebulizer jet also includes a convex fractionating surface, located outside the chamber and in the flow from the outlet port. The fractionating surface breaks the impacting flow of gas and liquid into a fine aerosol. For optimal nebulization, the jet inlet port and the outlet port are axially aligned and the jet inlet port is substantially smaller in diameter than the outlet port.

Disposable plastic nebulizer jets prior to this invention have been produced either as sets of separately molded parts, which must then be assembled into working devices, or as one-piece moldings. For nebulizer jets consisting of multiple parts, production and packing costs tend to increase proportionately with the number of parts. In addition, the time taken to assemble a nebulizer jet of this type is relatively long, since improper assembly could easily cause misalignment of the jet inlet and outlet ports, and degradation of nebulizer performance.

The molding process by which one-piece nebulizer jets were produced prior to this invention was a cumbersome one in some respects, involving the extraction of a number of mold pins from a single molded part. Extraction of the pins leaves intersecting passages in the molded part, to serve as the nebulizer chamber and as the inlet and outlet ports. In order to form the intersecting passages, the mold pins must be extracted from the part in non-parallel directions, and are therefore, subject to rapid wear. Moreover, the resultant fluid passages can not always be formed accurately and without surface flaws. Extraction of the mold pins sometimes scars the interior walls of the nebulizer, leaving burrs and dents that hinder optimal nebulization. These problems have largely discouraged the manufacture of nebulizer jets of one-piece construction.

Accordingly, there has existed a definite need for a molded one-piece disposable nebulizer jet that is economical to produce and package, easy to assemble, and also meets the structural requirements for optimal nebulization. The present invention satisfies this need.

SUMMARY OF THE INVENTION

The present invention resides in a novel one-piece nebulizer jet which, in an unassembled configuration, is a unitary structure perforated by parallel holes and shaped to define complementary parts located on opposite sides of integral hinge means. To assemble the nebulizer jet, the complementary parts are rotated relative to each other about the hinge means, and joined together in an assembled configuration. The parts are shaped to interlock or tightly engage each other in the assembled configuration. The new nebulizer jet offers the advantages of economy of production and ease of assembly without jeopardizing quality of performance.

More specifically, in one presently preferred embodiment of the invention the unitary structure is molded as first and second complementary parts arranged on opposite sides of the integral hinge means. The first complementary part has a jet inlet tube formed integrally with it to define a jet inlet port. The second complementary part has a liquid inlet tube formed integrally with it to define a liquid inlet port. The second complementary part is also perforated by a hole, to define an outlet port having its axis parallel to those of the jet and liquid ports.

The nebulizer jet may also include fractionating means formed integrally with the first and second complementary parts and joined to the second part by a second integral hinge means. Adjoining the fractionating means is an integral locking element shaped to engage the liquid inlet tube and hold the fractionating means in an operative position adjacent to the outlet port.

In an alternate embodiment of the invention, the first complementary part includes an integral jet inlet tube and an integral liquid inlet tube, and the second complementary part includes the outlet port and an integral post for retaining the fractionating means in its operative position. The second hinge means is joined to the post, which also serves to engage the integral locking element that adjoins the fractionating means.

An important advantage of the invention is that, since the central axes of the ports and tubes are parallel, the unassembled structure can be molded economically and to a high degree of precision. The required holes defining the ports to the nebulizer chamber are produced by means of molding pins that are extracted in parallel directions. Parallel pin extraction reduces wear on the pins, lowers the cost of production, and ensures a more precisely formed part, with its interior walls free of burrs and dents.

Ease of assembly is another of the invention's advantages. Assembly is achieved by rotating the first and second complementary parts relative to each other about the first integral hinge means, until the parts engage each other to form an enclosure. In the assembled configuration, the jet inlet port and the outlet port share a common central axis. Assembly is completed by rotating the fractionating means relative to the second integral hinge means, until it is secured in the operative position adjacent the outlet port. For optimal nebulizing action, the jet inlet tube is tapered to a smaller internal diameter toward the chamber. The outlet port has a cross-sectional area substantially larger than that of the jet inlet port.

Other aspects and advantages of the present invention will become apparent from the following detailed description, taken in conjunction with the accompanying drawings.

BRIEF DESCRIPTION OF THE DRAWINGS

FIG. 1 is a perspective view of an unassembled nebulizer jet produced in accordance with a preferred embodiment of the invention;

FIG. 2 is simplified elevational view of the nebulizer jet shown in FIG. 1, showing how integral parts of the jet are assembled;

FIG. 3 is a sectional view of a nebulizer assembly incorporating the nebulizer jet of FIGS. 1 and 2;

FIG. 4 is an enlarged sectional view of the nebulizer jet taken substantially along 4—4 of FIG. 3;

FIG. 5 is an enlarged, fragmentary sectional view of the nebulizer jet, showing a jet inlet port and an outlet port;

FIG. 6 is a perspective view of an unassembled nebulizer jet produced in accordance with a second embodiment of the invention; and FIG. 7 is a sectional view of another nebulizer assembly, incorporating the nebulizer jet of FIG. 6.

DESCRIPTION OF THE PREFERRED EMBODIMENTS

As shown in the drawings for purposes of illustration, the present invention is concerned with nebulizers, and particularly with the construction of disposable nebulizer jets for use in respirators. A nebulizer jet creates a fine aerosol spray of a liquid medicinal substance, to be added to a flow of breathing gas supplied to a patient undergoing respiration therapy.

A nebulizer jet has a chamber into which the liquid is drawn through one tube and an air or other gas jet is introduced through another tube. The jet passes through the chamber to an outlet port, and draws gas and liquid with it. The nebulization process is completed when the liquid impacts a fractionating surface outside the chamber. Nebulizer jets of the prior art are either produced as sets of separate component parts that have to be assembled with some care, or as single-piece devices. One-piece nebulizer jets have been difficult to produce in quantity and with precision, principally because of the necessary arrangement of passages intersecting the chamber.

In accordance with the invention, a one-piece nebulizer jet, indicated generally by reference numeral 10 (FIG. 1), is formed in an unassembled configuration of at least two hinged complementary parts 12 and 14, which are folded together to form an assembled nebulizer jet, as shown in FIG. 3. The first part 12 takes the shape of an elongated cup open in the downward direction (as viewed in FIG. 1) and having a relatively flat top wall 12*a* and a continuous sidewall 12*b*. The second part 14 also takes the shape of an elongated cup, sized to engage and fit tightly in the first part 12. The second part 14 also has a relatively flat top wall 14*a* and a continuous sidewall 14*b*.

Joining the parts 12 and 14 is a thinned-out section 16 that serves as a hinge. The hinge section 16 joins with the first part 12 at one rounded end portion of the sidewall 12*b* and adjacent to the open bottom of the part. The hinge section 16 joins with the second part 14 also at a rounded end portion of the continuous side wall 14*b*, but near the top wall 14*a*.

When the two parts 12 and 14 are rotated one relative to the other, as shown by the arrow 20 in FIGS. 1 and 2, the second part 14 engages in the first part 12 and forms a nebulizer chamber 22 (FIG. 3). Use of the hinge section 16 and snugly fitting complementary parts 12 and 14 ensures that the nebulizer components align themselves quickly and easily.

In the FIG. 1 embodiment, the first part 12 of the nebulizer jet includes a jet inlet tube 30 formed integrally with the top wall 12*a*. As best shown in FIG. 5, the tube 30 terminates in a reduced-diameter passage 32 that serves as a jet inlet port to the chamber 22. The other part 14 includes an outlet port 34 in the top wall 14*a*. As seen in FIG. 5, the outlet port is located directly opposite the jet inlet port 32 and is of substantially greater diameter than the jet inlet port. Also integral with the top wall 14*a* of the second part 14 is a liquid inlet tube 36, the bore of which penetrates the top wall 14*a* and communicates with the chamber 22.

The same principle of hinged complementary parts is used to provide a fractionating mechanism, in the form of a fractionating ball 40. The ball 40 is practically hemispherical in shape, and is molded integrally with the first and second parts 12 and 14 of the nebulizer jet 10. The ball 40 is connected by its flat underside to an integral arcuate element 42, which in turn is connected to one end of a vertical hinge section 44, the other end of which is integrally formed with the liquid inlet tube 36. The ball 40 and arcuate element 42 can be rotated together about the hinge section 44, as indicated by the arrow 48, until the arcuate element engages and is secured to the liquid inlet tube 36. In this position, the ball 40 is positioned immediately adjacent to the outlet port 34, and functions to fractionate liquid emerging from the outlet port into an aerosol of very small liquid particles.

The nebulizer jet 10 in its assembled configuration is employed in a nebulizer assembly 50 (FIG. 3). The assembly 50 includes an inlet tube connector 52 and an outlet tube connector 53, both adapted for connection to respirator tubes (not shown), and formed as a single integral structure allowing for fluid flow from inlet connector to outlet connector. A liquid reservoir jar 54 is removably secured beneath the integral connector structure, which has an opening 56 into the jar. The assembled nebulizer 20 is supported in the jar 54 with its liquid inlet tube 36 oriented down into the jar and its jet inlet tube 30 oriented up and extending through the structure of the connectors 52 and 53, for connection to a pressurized gas supply, as indicated at 58. Nebulized liquid accumulates above the liquid in the jar 54, and is swept into the flow through the connectors 52 and 53.

The alternative embodiment of the nebulizer 10' shown in FIG. 6 also has first and second complementary parts 12' and 14', which engage in an assembled configuration in the same way as the FIG. 1 embodiment. The only significant difference is that the first part 12' has an integral liquid supply tube 36', as well as a jet supply tube 30'. A fractionating ball 40' is molded integrally with the second part 14' and is connected to the second part by an arcuate element 42' and a hinge section 44'. Since the liquid supply tube 36' is not on the second part 14', a post 64 is provided in the same position as the liquid supply tube 36 in the FIG. 1 embodiment. The hinge section 44' is integrally formed with the post 64. In the assembled configuration, the arcuate element 44' engages the post 64 to secure the fractionating ball 40' in its operative position, as shown in FIG. 7.

The FIG. 6 embodiment of the nebulizer jet 10' is installed in a nebulizer 50' of the type shown in FIG. 7. The nebulizer 50' includes an inlet tube connector 52' adapted for connection to an air or gas supply tube (not shown), and an outlet tube connector 53' adapted for connection to a patient breathing tube (not shown), the two connectors being formed as a single piece, together with an intermediate tubular section 66. A liquid reservoir jar 54' is removably secured to the underside of the intermediate section 66, which has an opening 56' to provide fluid communication between the connectors 52' and 53' and the jar 54'. A gas jet supply tube 58' enters the jar 54' from beneath, through an off-center opening in the jar. The jet inlet tube 30' of the nebulizer jet 10' is coupled to the gas jet supply tube 58', and supports the nebulizer jet in the jar 54' with the liquid supply tube 36' in a practically central position in the jar. The liquid supply tube 36' extends partially into a small recess or well 68 at the bottom of the jar 54', to ensure maximum use of the liquid capacity of the jar.

The nebulizer jet 10' operates in the same manner as the first-described jet 10. Liquid is drawn into the nebulizer chamber 22', swept through the outlet port 34' and fractionated upon impact with the fractionating ball 40'. Nebulized liquid is then drawn into the breathing gas supply flowing through the tube connectors 52' and 53'.

It will be appreciated from the foregoing that the present invention represents a significant advance in the field of nebulizers. In both illustrated embodiments, the use of hinged complementary parts greatly facilitates both fabrication and assembly of nebulizer jets. Optimal nebulization can be easily achieved, since alignment of the jet inlet port and the outlet port is automatic and fluid passages in the device can be formed to a high degree of precision. It will also be appreciated that, although specific embodiments of the invention have been described in detail for purposes of illustration, various modifications may be made without departing from the spirit and scope of the invention. Accordingly, the invention is not to be limited except as by the appended claims.

I claim:

1. A one-piece nebulizer jet, comprising:
first and second complementary components each defining complementary contours of a nebulizer chamber, said components having openings in them to provide a jet inlet port, a liquid inlet port and an outlet port;
integral hinge means connecting said first and second complementary components and permitting said complementary components to be rotated with respect to each other into an assembled position;
integral means for holding said first and second complementary components in the assembled position, in which the jet inlet port and the outlet port are axially aligned;
fractionating means formed integrally with said first and second complementary components, and presenting a convex surface to the flow of fluid from the outlet port;
second integral hinge means connecting said fractionating means with one of said first and second complementary components and permitting rotation of said fractionating means to an operative position adjacent to the outlet port; and
integral retaining means, for retaining said fractionating means in its operative position, and including an arcuate element adjoining said fractionating means, and an integral post for engaging said arcuate element as said fractionating means reaches the operative position.

2. A one-piece nebulizer jet, comprising:
first and second complementary components each defining complementary contours of a nebulizer chamber, said components having openings in them to provide a jet inlet port, a liquid inlet port and an outlet port;
integral hinge means connecting said first and second complementary components and permitting said complementary components to be rotated with respect to each other into an assembled position;
integral means for holding said first and second complementary components in the assembled position, in which the jet inlet port and the outlet port are axially aligned;
fractionating means formed integrally with said first and second complementary components;
second integral hinge means connecting said fractionating means with one of said first and second complementary components and permitting rotation of said fractionating means to an operative position adjacent to the outlet port; and
integral retaining means, for retaining said fractionating means in its operative position, and including an arcuate element adjoining said fractionating means and an integral post on said second complementary component, for engaging said arcuate element in the operative position of said fractionating means;
and wherein said first complementary component includes openings for the jet inlet port and the liquid inlet port, and said second complementary component includes an opening for the outlet port.

3. A one-piece nebulizer jet, comprising:
first and second complementary components each defining complementary contours of a nebulizer chamber, said components having openings in them to provide a jet inlet port, a liquid inlet port and an object port;
integral hinge means connecting said first and second complementary components and permitting said complementary components to be rotated with respect to each other into an assembled position;
integral means for holding said first and second complementary components in the assembled position, in which the jet inlet port and the outlet port are axially aligned;
fractionating means formed integrally with said first and second complementary components;
second integral hinge means connecting said fractionating means with one of said first and second complementary components and permitting rotation of said fractionating means to an operative position adjacent to the outlet port; and
integral retaining means, for retaining said fractionating means in its operative position;
and wherein
said first complementary component includes an opening for the jet inlet port,
said second complementary component includes openings for the outlet port and the liquid inlet port, and
said integral retaining means includes an arcuate element adjoining said fractionating means and an integral liquid inlet tube communicating with the liquid inlet port, for engaging said arcuate element in the operative position of said fractionating means.

* * * * *

UNITED STATES PATENT AND TRADEMARK OFFICE
CERTIFICATE OF CORRECTION

PATENT NO. : 4,509,688
DATED : April 9, 1985
INVENTOR(S) : Roger A. Gagne

It is certified that error appears in the above-identified patent and that said Letters Patent are hereby corrected as shown below:

Column 2, line 16, after the word "liquid" insert the word --inlet--.

Claim 3, line 6, delete the word "object" and insert therefor the word --outlet--.

Signed and Sealed this

Third Day of September 1985

[SEAL]

Attest:

DONALD J. QUIGG

Attesting Officer        Acting Commissioner of Patents and Trademarks - Designate